United States Patent [19]

Pemawansa et al.

[11] Patent Number: 4,961,852
[45] Date of Patent: Oct. 9, 1990

[54] POLYALDEHYDE ACTIVATED MEMBRANES

[75] Inventors: Kanyawasam P. W. Pemawansa, Ann Arbor; Mark Heisler, Saline; Menahem Kraus, Ann Arbor, all of Mich.

[73] Assignee: Gelman Sciences, Inc., Ann Arbor, Mich.

[21] Appl. No.: 321,282

[22] Filed: Mar. 9, 1989

Related U.S. Application Data

[62] Division of Ser. No. 96,730, Sep. 14, 1987, Pat. No. 4,824,870.

[51] Int. Cl.$^5$ ............... B01D 29/00; B01D 29/46; B01D 39/00
[52] U.S. Cl. ............... 210/490; 210/500.22; 210/500.27; 210/500.34; 210/500.35; 210/500.41; 210/500.42; 210/500.43; 521/53; 521/54
[58] Field of Search ............... 521/53, 54, 134, 136; 210/500.22, 500.27, 490, 500.34, 500.35, 500.41, 500.42, 500.43

[56] References Cited

U.S. PATENT DOCUMENTS

| 3,770,588 | 11/1973 | Forgione | 195/63 |
|---|---|---|---|
| 3,821,083 | 6/1974 | Van Leemputten et al. | 195/63 |
| 3,977,941 | 8/1976 | Vieth et al. | 195/63 |
| 4,066,512 | 1/1978 | Lia et al. | 195/127 |
| 4,229,188 | 10/1980 | Intille | 55/16 |
| 4,229,537 | 10/1980 | Hodgins et al. | 435/177 |
| 4,238,204 | 12/1980 | Perry | 55/16 |
| 4,255,591 | 3/1981 | Makin et al. | 55/16 |
| 4,279,787 | 7/1981 | Huizinga | 260/8 |
| 4,352,884 | 10/1982 | Nakashima et al. | 435/180 |
| 4,357,142 | 11/1982 | Schall, Jr. et al. | 23/230 |
| 4,361,484 | 11/1982 | Larsson et al. | 210/632 |
| 4,363,634 | 12/1982 | Schall, Jr. | 23/230 |
| 4,418,152 | 11/1983 | Hosaka et al. | 436/511 |
| 4,438,239 | 3/1984 | Rembaum et al. | 525/54.1 |
| 4,511,478 | 4/1985 | Nowinski et al. | 210/691 |
| 4,612,118 | 9/1986 | Kamiyama et al. | 210/490 |
| 4,624,923 | 11/1986 | Margel | 435/176 |
| 4,657,873 | 4/1987 | Gadow et al. | 436/532 |
| 4,661,526 | 4/1987 | Ford | 54/53 |

OTHER PUBLICATIONS

Y. Chen, S. Mason & R. E. Sparks, "Collagenase Immobilized on Cellulose Acetate Membranes", Biomaterial: Interfacial Phenomena and Applications, pp. 484–491, 1982.
Shlomo Margel, "Polyacrolein Microspheres", Methods in Enzymology, vol. 112, 1985, pp. 164–175.
"Soluble-Insoluble Complex of Trypsin Immobilized on Acrolein-Acrylic Acid Copolymer", Biotechnology and Bioengineering, vol. XVIII (1976).

Primary Examiner—Morton Foelak
Attorney, Agent, or Firm—Krass & Young

[57] ABSTRACT

An activated microporous membrane is provided, having aldehyde functional groups on its inner and outer surfaces. The aldehyde functionality on all surfaces provides for effective covalent bonding to the membrane by amine containing materials. The activated membrane can be made of a polysulfone/polyacrolein mixture or a polysulfone microporous membrane treated with a polyacrolein solution.

7 Claims, No Drawings

POLYALDEHYDE ACTIVATED MEMBRANES

This application is a copending divisional application of U.S. Ser. No. 096,730, filed Sept. 14, 1987, now issued as U.S. Pat. No. 4,824,870 dated Apr. 24, 1989.

BACKGROUND OF THE INVENTION

This invention relates generally to chemically activated microporous membranes. More particularly, this invention relates to polyaldehyde activated microporous membranes and a process for making the same.

Aldehydes have been used in conjunction with a variety of materials, such as beads and microspheres. In addition, substrates including certain membranes have been chemically activated with aldehyde functional groups using methods such as oxidation.

Microporous membranes are also known. The traditional use of microporous membranes to filter materials has been based mainly on their physical properties, e.g., pore size, thickness, strength, etc. For example, retention by microfiltration membranes is accomplished mainly through mechanical sieving. Even in uses where the chemical properties of a membrane come into play, such as in gas separation or desalination, generally chemical bonding between the separated species and the membrane matrix is not employed.

A type of microporous membrane which is capable of reacting chemically with soluble or suspended species is the so-called "affinity membrane." Various affinity membranes are commercially available. Some, which are designed to interact specifically with only one or a few species in complicated mixtures, are improvements over traditional membranes which rely on physical separations. Examples of such highly specific interactions include antigen/antibody, hapten/antibody, apoprotein/cofactor and lectin/carbohydrate. Affinity membranes may be used in immunodiagnostic testing wherein the interaction between the antigen and antibody is particularly relevant.

But the currently available affinity membranes have certain drawbacks. For some, shelf life is limited because the active groups are destroyed by prolonged exposure to the atmosphere. For others, binding capacity is limited. Nonspecific binding, which can lead to false positive readings, is a problem as well. Nonspecific covalent binding is typically remedied by treating the membrane with a blocking agent. However, blocking agents do not always solve the problem satisfactorily.

There are also various shortcomings in the methods for making activated membranes. For example, some of the methods are limited to certain substrates or membrane polymers. An oxidation reaction, for example, is limited to membranes such as cellulose acetate, and would not activate other commercial membranes such as polysulfone, nylon or polypropylene. Also other chemical reactions may damage the pore structure of certain species of microporous membranes. In still others, clogging of the pores may present a problem.

The drawbacks and shortcomings mentioned above illustrate some of the unsatisfactory characteristics of currently available affinity membranes and the need for further improvements in the art.

SUMMARY OF THE INVENTION

The present invention is directed to an activated microporous membrane and a process for making an activated microporous membrane. In a broad aspect, the invention includes an activated microporous membrane that comprises a membrane polymer and a polyaldehyde. The membrane polymer is physically activated with a mixture that contains polyaldehyde. A sufficient amount of polyaldehyde is combined with the membrane polymer to provide for effective covalent bonding with amine containing materials and other aldehyde reactive materials.

Various membranes of the present invention demonstrate excellent binding capacity, specificity and sensitivity. Without being bound to any particular theory, the effective binding capacity of the present membrane is believed to be due in part to the aldehyde functional groups which are attached to both the inner and outer surfaces of the microporous membrane. "Sensitivity" refers to the ability of the membrane to detect even small amounts of bound or attached species. "Specificity" means the ability of the membrane to selectively bind or filter certain species from complex mixtures.

A practical advantage of the present invention is that membranes can be produced that are reactive enough to react with typical nucleophiles such as amines but not so reactive that they suffer degradation by ambient moisture or oxygen. Thus, one aspect of the invention provides a membrane which has not only a high binding capacity and improved sensitivity but also a prolonged shelf life and ease of handling.

In one aspect, the membrane of this invention is polymeric and microporous, i.e., it includes a polymer and has an internal surface and an external surface. When the activated microporous membrane of the invention is contacted with a mixture that is to be filtered, the external portion of the membrane is immediately and directly exposed to the mixture. But the internal surface or interstices of the membrane are not immediately exposed. It is only after the membrane has been in contact with the mixture for a period of time that the internal surface is exposed to the mixture. These internal interstices or pore surfaces are collectively termed the "internal surface" of the membrane. This internal surface area has been found to be important to the success of the invention.

In one aspect, the activated membranes of this invention have a plurality of aldehyde functional groups substantially covering the internal and external surfaces. The interstices as well as the external surfaces are covered by an effective amount of aldehyde for activating the membrane. The number of aldehyde groups is sufficient for effective covalent bonding with amine containing materials and other aldehyde reactive groups.

The following detailed description describes the claimed invention in greater detail and discloses the preferred embodiment. The description, along with the examples and the rest of this disclosure, is addressed specifically to those skilled in the art, to enable them to make and to use the claimed invention.

DETAILED DESCRIPTION AND PREFERRED EMBODIMENT

In a broad aspect, the invention includes an activated microporous membrane that comprises a membrane polymer and a polyaldehyde. The polyaldehyde is physically combined with the membrane polymer in an amount sufficient to activate the membrane, i.e., to provide for effective covalent bonding by amine containing materials and other aldehyde reactive materials.

"Activating" or "combining" in this sense is a broad term that encompasses both (a) coating or treating a precast microporous membrane with the polyaldehyde; and (b) physically mixing the polyaldehyde with the membrane polymer before casting the membrane. The former is called "membrane post treatment" while the latter is called "precasting." "Physically combining" or "physically mixing" the polymer and the polyaldehyde means that there is a lack of significant chemical reaction between the polyaldehyde and the polymer.

In one specific embodiment, the invention comprises an activated microporous membrane in which substantially all the available surfaces of the membrane are coated by the polyaldehyde. The activated membrane thus contains sufficient polyaldehyde to provide effective aldehyde functionality on substantially all available surfaces, i.e., both the external and internal surfaces. The resulting free aldehyde groups covering substantially all exposed surface areas provide effective covalent bonding between the finished membrane of this invention and aldehyde reactive materials, such as amines, which contact the membrane.

In one embodiment, the membrane is a "supported" membrane. Other embodiments include unsupported membranes. A supported membrane is a membrane cast on a substrate, preferably a nonwoven fabric. Supported membranes are often considered to have better mechanical properties and ease of handling than unsupported membranes.

Generally, the polyaldehyde is dissolved in a solvent to form a mixture. The mixture is then physically combined with the membrane polymer by either membrane post treatment or precasting. After the activated microporous membrane is made, the solvent is generally removed by washing, although some residual solvent may remain.

In certain embodiments, the polyaldehyde mixture is concentrated enough to properly activate the membrane. The membrane material, on the other hand, is sturdy and of sufficient chemical resistance to remain porous and substantially undamaged by the polyaldehyde containing mixture.

Membrane Post Treatment

In the preferred embodiment, the microporous membrane is first cast from the membrane polymer, then activated by physically coating or treating the cast membrane with the polyaldehyde containing mixture. This physical combination does not include any significant chemical reaction, such that would cause potential damage to the pore structure.

Polyaldehydes in general are contemplated for use in this invention. Preferably, the polyaldehyde chosen will be sufficiently soluble in the solvent to provide a true solution to avoid, for example, undesirable dispersions which could cause ineffective coating of the membrane surfaces. Polyaldehydes which have been found especially useful in the practice of the invention include polyacrolein and acrolein copolymers.

It has been found that the concentration of the solvent, in which the polyaldehyde dissolves, is important. If the solvent is not concentrated enough, it will not form a true solution with the polyaldehyde. If the solvent is too concentrated, it could damage the membrane pore structure of certain membranes. Accordingly, the solvent concentration should be reduced to avoid damaging the membrane. This can be done by diluting the solvent concentration with, for example, water or alcohol, which will reduce the solvent concentration yet still dissolve the polyaldehyde.

Where polyacrolein is employed, a strong solvent such as pyridine or dimethyl formamide (DMF) is used to dissolve the polyacrolein. One embodiment of the post treatment mode comprises a microporous membrane treated with pure polyacrolein dissolved in DMF or pyridine. At high concentrations DMF or pyridine damages the pore structure of polysulfone. Accordingly, for polysulfone, an effective DMF solution in a polyacrolein containing mixture has about 60 percent DMF and about 40 percent water. Example 6 shows one operative range of DMF solvent concentrations. Other membrane polymers, such as those made from nylon or polypropylene, are generally not sensitive to pore damage and can be successfully coated with polyacrolein without regard to the solvent concentration.

One polyaldehyde which has been found to work well with polysulfone membranes is a copolymer of acrolein, e.g., hydroxyethyl methacrylate acrolein copolymer. This copolymer is more soluble in solvents such as DMF and pyridine than is pure polyacrolein. Thus a less concentrated solvent can be used to avoid any potential damage to the membrane pore structure.

The proportionate amounts of polyaldehyde and solvent are also important. Enough polyaldehyde should be present to sufficiently activate the membrane. Further, enough solvent must be employed to dissolve the polyaldehyde. It is contemplated that from about 0.2 weight percent to about 10 weight percent polyaldehyde per volume of solution is adequate.

PRECASTING TREATMENT

Another embodiment provides for the activation membrane polymer prior to casting. This may be referred to as the precasting treatment. In this embodiment, the polyaldehyde and the membrane polymer are physically mixed before casting. There should be sufficient polyaldehyde to activate the membrane polymer. With polyacrolein, weight ratios of from about 1:5 to about 1:1 polyacrolein to membrane polymer are appropriate.

The invention is not strictly limited to a particular species of microporous membrane. However, selection of an appropriate membrane polymer is important to achieve maximum effectiveness. Generally speaking, the species of membrane polymer must be able to withstand the solvent system that comprises the polyaldehyde. Examples of suitable membrane polymers include polysulfone and polyacrylonitrate-vinyl chloride copolymer. Other membranes, such as nylon, cellulose acetate, polyvinylidene fluoride, polypropylene, and glass fibers, could also be expected to work.

Membrane materials which would swell or dissolve from contact with the polyaldehyde containing mixture are undesirable. However, this depends to some extent on the concentration of the solvent used for the polyaldehyde. For example, concentrated DMF on a polysulfone membrane causes damage to the membrane. Consequently, it is preferable to use a more soluble polyaldehyde such as a copolymer of acrolein and hydroxyethyl methacrylate with polysulfone microporous membrane. No significant damage of polysulfone membrane pore structure has been encountered with this copolymer solvent system.

POLYMERIZATION

Polymerization conditions are also important. For example, under certain conditions polymerization will involve the aldehyde group of acrolein, and the resulting polymer will therefore have very little, if any, aldehyde functionality.

Where a polyaldehyde copolymer is formed between an acrolein monomer and hydroxyethyl methacrylate, free radical copolymerization is preferred, using a proper conventional initiator such as peroxide. In contrast, if the reaction is done under the influence of base-catalyzed initiators, such as sodium hydroxide, few if any free aldehydes are formed. Likewise, if ionizing radiation is used, microspheres will be formed, which may not be able to penetrate all interstices of the porous membrane.

Generally, the preferred polymerization conditions are those which provide a highly soluble and highly functional polymer mixture that will cover the microporous membrane efficiently and without damage to or clogging of the pore structure. The polyaldehyde of the present invention is soluble enough in solutions having solvents such as DMF or pyridine to penetrate substantially all pores or interstices of the microporous membrane structure.

In one embodiment of this invention, the aldehyde functional groups are attached by admixing the membrane polymer with an effective amount of the polyaldehydecontaining mixture. Generally speaking, the type and amount of polyaldehyde containing mixture vary the binding effectiveness of the membrane. These are discussed below.

A preferred embodiment which has good solubility but which does not damage the pore structure of a polysulfone membrane is an acrolein copolymer. However, incorporation of a comonomer with acrolein may somewhat reduce the concentration of the reactive aldehyde groups. Accordingly, selection of the comonomer is important. A good balance of solubility and high reactivity is found with the copolymers of acrolein and hydroxyethyl methacrylate. The Process Another broad aspect of the invention is the process for making the activated microporous membrane, which basically comprises an activating step and a casting step. More particularly, the activating step refers to activating the membrane polymer by mixing, treating or combining a polyaldehyde with the membrane polymer. The casting step comprises casting the microporous membrane itself which includes the membrane polymer.

The actual method for casting microporous membranes is conventional. In the preferred embodiment, the casting step is performed first. Here, the microporous membrane matrix is cast from a membrane polymer system, which may include polymers such as polysulfone, polyacrylonitrilevinyl chloride, nylon, polyvinylidene fluoride and polypropylene. The matrix may also include glass fibers. Preferably, the pore sizes of the microporous membrane are between about 0.1 and about 10 microns in diameter. These have been found sufficiently porous for most applications.

After the casting of the membrane, the activating or treating step is performed. Here, the polyaldehyde is physically combined with the cast microporous membrane. Preferably, a dilute solution of the polyaldehyde containing mixture is made in a solvent that is not harmful to the membrane polymer system. A harmful solvent is generally one that would increase the solubility of the membrane to a point where it would damage the membrane by causing the pore structure to collapse. As discussed above, the preferred solvent is an aqueous DMF solution having at most about 60% DMF. Pyridine may also be used as a solvent.

One of the embodiments includes copolymerizing acrolein with hydroxyethyl methacrylate to obtain a copolymer, then mixing with a solvent to obtain a mixture having the appropriate concentration and solubility. The membrane is dipped in this mixture in a manner ensuring proper wetting of all surfaces, internal and external. Once dried, the membrane is ready for use.

In another embodiment of this process, the activating step is performed first. In this embodiment, the polyaldehyde is physically mixed with the microporous polymer prior to casting. A polyaldehyde containing mixture is physically mixed with a membrane polymer in the proper proportions. Using this mixture, a membrane matrix is cast in a conventional manner. When the membrane has undergone transition from a liquid or sol phase to a solid or gel phase and subsequently dried, the pore surfaces of the membrane will have aldehyde functionalities available for reaction.

The following reaction steps illustrate how acrolein is polymerized. As indicated, acrolein can be polymerized either through the aldehyde group or the carbon-carbon double bond, depending on polymerization conditions.

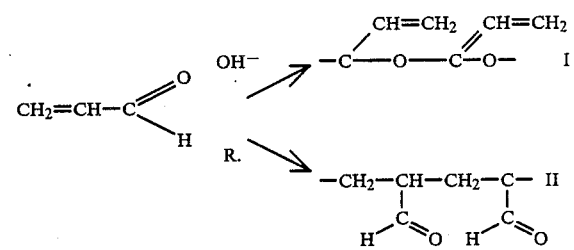

The resulting polymer is therefore one having either pendant vinyl (I) or aldehyde (II) groups. Polymer II is suitable for a cast membrane in the presence of a solvent system or alternatively for blending in a membrane forming mix so as to activate the membrane before casting. As discussed above, it is preferable to improve the solubility of the aldehyde polymer so that a larger variety of membranes can be treated.

The activated microporous membrane can be used in a variety of applications. It is particularly effective as a binding matrix. Various amine containing macromolecules will attach to it covalently. The membrane can therefore be used for selectively binding proteins, nucleic acids and other nucleophiles. The bound species can then be used in a variety of uses such as catalysis and analysis.

The invention will be further clarified by a consideration of the following examples, which are intended to be purely exemplary of the use of the invention.

EXAMPLES

EXAMPLE 1

Polymerization of Acrolein

A mixture containing freshly distilled acrolein (50 ml, 0.749 moles), benzoyl peroxide (2 g, 8.2 b m.moles) and 250 ml of dimethyl formamide (DMF) was purged for 3 hours with nitrogen at room temperature. Then the mixture was heated to 70°-80° C. for 2 hours with stirring. The resulting solution was stirred at room temperature for 15 hours. A yellowish homogeneous solution was obtained. This solution was diluted with water to obtain polyacrolein as a white precipitate. Polyacrolein was redisolved in pyridine and stored at room temperature for use in Example 2.

EXAMPLE 2

Activation of a Membrane By Coating a Polysulfone Microporous Membrane with Polyacrolein Mixture The polyacrolein/pyridine solution of Example 1 was heated to 70° C. and diluted with 1 volume of boiling water. This polyacrolein containing mixture was applied on a polysulfone microporous membrane at 70° C. and dried at room temperature in air. No sign of clearing (destruction of porous structure) of the membrane was observed by the above treatment. This indicated that the mixture solvent was not too strong.

EXAMPLE 3

Activation of a Membrane by Precasting with a Polyacrolein Mixture

The polyacrolein/DMF solution in Example 1 was mixed with polysulfone to precast a microporous membrane. The casting mix was prepared by blending 30 g of the polyacrolein solution, 10 ml of additional DMF, 10 g of polyethylene glycol, 1.5 g of polyvinyl pyrrolidinone, and 8.5 g of polysulfone. The mix was cast on a glass plate at room temperature and stored in a humidity chamber to cause pore formation. The microporous membrane produced by this method exhibited a water flow rate of 6.8 sec/100 ml/9.62 $cm^2$ and a water bubble point of 18 psi. This indicated that the membrane was microporous and possessed an adequate pore structure.

EXAMPLE 4.

Copolymerization of Acrolein and Hydroxyethyl Methacrylate

Hydroxyethyl methacrylate acrolein copolymer was dissolved in DMF and diluted with water. One such mixture was made in the following manner. A mixture consisting of freshly distilled acrolein (50 ml, 0.749 moles), hydroxyethyl methacrylate (15 ml, 0.12 moles), benzoyl peroxide (3.25 g, 13.4 m.moles) and 200 ml of DMF was purged with nitrogen for 1 hour and then refluxed for hour. The resulting mixture was stirred at room temperature for 15 hours. A yellow copolymer solution was obtained. This copolymer solution was diluted with 1.5 volume of water without any solidification.

EXAMPLE 5

Activation of a Polysulfone Membrane By Coating a Microporous Membrane with a Copolymer Mixture:

The copolymer solution of Example 4 was heated to 70° C. and diluted with 1.5 volumes of water at 70° C. This copolymer solution was applied on a supported microporous polysulfone membrane at room temperature and dried in air at room temperature. No sign of clearing of the membrane was observed by this treatment. Further, the supported polysulfone membrane exhibited a water flow rate of 13.5 sec/100 ml/9.62 $cm^2$ after the above treatment. This indicated that the hydroxyethyl methacrylate acrolein copolymer mixture did not significantly damage the pore structure of the microporous membrane.

EXAMPLE 6

Copolymerization of Acrolein and Hydroxyethyl Methacrylate

In order to demonstrate the usefulness of this invention with different membranes, a second copolymer mixture was made and applied to a polysulfone microporous membrane and an acrylonitrile/vinyl chloride copolymer microporous membrane.

First, a mixture of freshly distilled acrolein (265 ml, 3.97 moles), hydroxyethyl methacrylate (62 ml, 0.49 moles), benzoyl peroxide (17 g, 70 m.moles) and DMF (1060 ml) was purged with N2 gas for 6 hours. This mixture was then heated to 95° C. for 22 hrs. The final concentration of the copolymer was 17.5% (w/v). A brown copolymer solution was stored at room temperature for membrane post treatment.

EXAMPLE 7

Activation of Polysulfone and Polyacrylonitrile-Vinyl Chloride Microporous Membranes by Coating The copolymer solution in Example 6 was diluted with a mixture of 1:1:1 DMF/water/isopropanol to form various copolymer solutions including 0.5%, 1%, 2%, 3%, 4% and 5% (w/v) solutions. These copolymer solutions were applied to a polysulfone microporous membrane and a polyacrylonitrile-vinyl chloride membrane.

The membranes were quenched in deionized water, washed a few times with deionized water, and dried at 70° C. The flow rates of two of the membranes, i.e., those treated with the 4% solution, were measured. It was found that the water, flow rates of the membranes were reduced. For instances, the flow rate of the treated polysulfone membrane was reduced from 10.7 sec/100 ml/9.62 $cm^2$/572 mm Hg to 13.1 sec/100 ml/9.62 $cm^2$/572 mm Hg. This reduction in flow rates indicated that the internal surfaces of the membranes were coated. The flow rates of the treated membranes are found in Table 1. The binding capacities of these membranes are shown in Example 8.

TABLE 1

| Water Flow Rates of Composite Membranes | |
| --- | --- |
| Membrane | Water Flow Rate sec/100 ml/9.2 $cm^2$/572 mm Hg |
| Polysulfone membrane coated with aldehyde polymer in Example 7. | 13.1 |
| Acrylonitrile/vinyl chloride copolymer supported membrane coated with aldehyde polymer in Example 7. | 16.6 |

EXAMPLE 8

As demonstrated by the following data, several embodiments of this invention showed excellent binding capacities.

TABLE 2

| Total Protein Binding Capacity (ug/$cm^2$) of the Membranes by ELISA | |
| --- | --- |
| Membrane | Total Binding Capacity (ug/$cm^2$) |
| Polysulfone membrane coated with aldehyde polymer in Example 7. | 96 |
| Acrylonitrile/vinyl chloride copolymer supported membrane coated with aldehyde | 106 |

TABLE 2-continued

Total Protein Binding Capacity (ug/cm$^2$) of the Membranes by ELISA

| Membrane | Total Binding Capacity (ug/cm$^2$) |
|---|---|
| polymer in Example 7.[a] | |

[a] 2¼ hr. binding time at 35° C.

EXAMPLE 9

Another embodiment of the invention comprising glyoxyl agarose polyaldehyde, was made to demonstrate the further usefulness of the invention. A solution was prepared, mixing 0.5 g glyoxyl agarose (NuFix TM manufactured by FMC Corporation) in 200 ml of boiling water. The solution was used to treat a polysulfone membrane in the same manner as in Example 5. It was observed that the flow properties of the membrane remained unchanged indicating that the pore structure remained essentially undamaged.

EXAMPLE 10

As demonstrated by the following data, the membranes of this invention showed specificity and binding capacity that was superior to other commercially available membranes. Commercial Affinity Membrane A was a nylonbased membrane sold by Pall Corporation under the name Biodyne. Commercial Affinity Membrane B was a polyvinylidene difluoride-based membrane sold by Millipore Corp. under the name Immobilon.

TABLE 3

Total Binding Capacities (ug/cm$^2$) of Membranes by BCA Method
(Total binding capacity = covalent or permanently bound protein + loosely bound or noncovalent bound protein per cm$^2$)

| Membrane | Total Binding Capacity (ug/cm$^2$) | Non-Covalently Bound Protein (ug/cm$^2$) |
|---|---|---|
| Commercial Affinity Membrane A | 57 | 10 |
| Commercial Affinity Membrane B | 42 | Not Detectable (10) |
| Nitrocellulose[a] | 94 | 64 |
| Polysulfone Membrane Coated with Aldehyde Polymer, from Example 5[b] | 120 | Not Detectable (10) |
| Polysulfone/Aldehyde Polymer Microporous Membrane in Example 7[a] | 90 | Not Detectable (10) |
| Polysulfone Supported Membrane Coated with Aldehyde Polymer in Example 7[b] | 125 | 5.2 |
| Polysulfone Membrane Coated with Aldehyde Polymer in Exampe 7[b] | 148 | 3.4 |
| Polysulfone Membrane Coated with Aldehyde Polymer in Example 2[d] | 87 | |

[a] 1 hour binding time at room temperature.
[b] 1 hour binding time at 60° C.
[c] 3 hours binding time at room temperature.
[d] 3.45 hours binding time at room temperature.

These binding capacities were determined according to the BCA method, developed by P. K. Smith, et. al., *Analytical Biochemistry*, 150, page 76 (1985).

What is claimed is:

1. An affinity membrane comprising:
   a microporous polymeric membrane matrix with available surface areas including an internal surface area comprising internal pore surfaces and internal interstices, and an external surface area; and
   polyaldehyde having physically bound aldehyde functional groups which are thus bound without significant chemical reaction to substantially all said available surface areas, said polyaldehyde further having unbound aldehyde groups that are free to react with an have an affinity for aldehyde reactive materials, said unbound polyaldehyde groups being in an amount such that the affinity of the membrane for protein is characterized by enhanced specifity and total binding capacity.

2. An activated polymeric microporous membrane as recited in claim 1 wherein the pore surfaces have free aldehyde functionalities available for affinity reaction.

3. A membrane as recited in claim 1 wherein the matrix is a supported matrix.

4. A membrane as recited in claim 1 wherein the matrix is a supported matrix and the polyaldehyde is selected from the groups consisting of aldehyde-agarose, polyacrolein, and acrolein copolymer.

5. A membrane as recited in claim 1 wherein the matrix comprises polysulfone and the polyaldehyde is a copolymer of acrolein and hydroxyethyl methacrylate.

6. A membrane as reacted in claim 1 having a total binding capacity of at least about 10 ug/cm$^2$ based on the outer surface area of the membrane.

7. An activated microporous membrane as recited in claim 1, wherein:
   the microporous membrane is cast from a first mixture that includes a membrane selected from the group consisting of polysulfone, polyacrylonitrilevinyl chloride, nylon, polypropylene; and
   the microporous membrane is activated by physically mixing with the first mixture a second mixture that includes a member selected from the group consisting of polyacrolein and a copolymer of acrolein and hyroxyethyl methacrylate;
   wherein physically mixing the first mixture to the second mixture includes either post-treating the cast membrane or mixing the first mixture and the secónd mixture before casting.

* * * * *

UNITED STATES PATENT AND TRADEMARK OFFICE
CERTIFICATE OF CORRECTION

PATENT NO.   :   4,961,852
DATED        :   October 9, 1990
INVENTOR(S)  :   Kanyawasam P. W. Pemawansa et al.

It is certified that error appears in the above-identified patent and that said Letters Patent is hereby corrected as shown below:

Column 5, line 37, "The Process" should be a heading;

Column 7, line 46, "for hour" should be --for 1 hour--;

Column 9, line 65, "Exampe" should be --Example--;

Column 10, line 29, "with an" should be --with and--;

Column 10, line 47, "as reacted" should be --as recited--.

Signed and Sealed this

Seventeenth Day of March, 1992

Attest:

HARRY F. MANBECK, JR.

*Attesting Officer*     *Commissioner of Patents and Trademarks*